United States Patent
Schick

(10) Patent No.: US 6,267,143 B1
(45) Date of Patent: Jul. 31, 2001

(54) SELECTION VALVE WITH FERRULE CLUSTER

(75) Inventor: Hans Gunther Schick, Concrete, WA (US)

(73) Assignee: Upchurch Scientific, Inc., Oak Harbor, WA (US)

(*) Notice: Subject to any disclaimer, the term of this patent is extended or adjusted under 35 U.S.C. 154(b) by 0 days.

(21) Appl. No.: 09/343,131

(22) Filed: Jun. 29, 1999

(51) Int. Cl.$^7$ .......................... F16R 11/074; F16L 39/00; G01N 1/10
(52) U.S. Cl. ................. 137/625.11; 137/625.46; 251/151; 285/124.1; 285/124.3; 73/863.73; 73/864.84
(58) Field of Search .......... 137/625.11, 625.46; 251/151; 285/124.1, 124.2, 124.3, 124.4, 124.5; 73/863.71, 863.72, 863.73, 864.84, 864.85, 864.86, 864.87

(56) References Cited

U.S. PATENT DOCUMENTS

| | | | |
|---|---|---|---|
| 1,881,913 | * 10/1932 | Parker | 285/124.4 |
| 2,846,246 | * 8/1958 | Peras | 285/124.3 |
| 3,469,863 | * 9/1969 | Riester et al. | 285/124.4 |
| 3,494,175 | 2/1970 | Cusick et al. . | |
| 3,752,167 | 8/1973 | Makabe . | |
| 3,868,970 | 3/1975 | Ayers et al. . | |
| 4,156,437 | * 5/1979 | Chivens et al. | 137/625.46 X |
| 4,182,184 | 1/1980 | Bakalyar et al. . | |
| 4,207,922 | * 6/1980 | Andrieux et al. | 137/625.11 |
| 4,242,909 | 1/1981 | Gundelfinger . | |
| 4,305,417 | * 12/1981 | Bell, Jr. | 137/625.11 X |
| 4,506,558 | 3/1985 | Bakalyar . | |
| 4,540,026 | * 9/1985 | Ellsworth | 137/625.11 X |
| 4,705,627 | 11/1987 | Miwa et al. . | |
| 4,722,830 | 2/1988 | Urie et al. . | |
| 4,792,396 | 12/1988 | Gundelfinger . | |
| 4,804,208 | * 2/1989 | Dye | 285/308 X |
| 4,825,908 | * 5/1989 | Tsuchihashi et al. | 137/625.46 X |
| 4,995,646 | * 2/1991 | Johnston et al. | 285/124.3 |
| 5,010,921 | * 4/1991 | Nohl | 137/625.46 |
| 5,193,581 | 3/1993 | Shiroto et al. . | |
| 5,207,109 | 5/1993 | Olsen . | |
| 5,222,168 | 6/1993 | Saito et al. . | |
| 5,317,271 | 5/1994 | Wentworth et al. . | |
| 5,366,620 | 11/1994 | Schick . | |
| 5,394,092 | 2/1995 | Wentworth et al. . | |
| 5,419,208 | 5/1995 | Schick . | |
| 5,419,419 | 5/1995 | Macpherson . | |
| 5,472,598 | 12/1995 | Schick . | |
| 5,482,628 | 1/1996 | Schick . | |
| 5,594,346 | 1/1997 | Stearns et al. . | |
| 5,601,115 | * 2/1997 | Broerman | 137/625.11 X |
| 5,621,180 | 4/1997 | Simon et al. . | |
| 5,674,388 | 10/1997 | Anahara . | |
| 5,732,739 | * 3/1998 | Ota | 137/625.46 |
| 5,744,100 | 4/1998 | Krstanovic . | |
| 5,803,117 | 9/1998 | Olsen et al. . | |
| 5,819,798 | * 10/1998 | Claflin et al. | 137/625.11 |
| 5,863,428 | 1/1999 | Ma et al. . | |

OTHER PUBLICATIONS

Declaration of Hans Gunther Schick with attached Exhibits A, B, and C, Signed Dec. 08, 1999.
*Operating Instructions for Type 50 Teflon Rotary Valves, Rheodyne, Incorporated*, printed in U.S.A. 4/94.

* cited by examiner

*Primary Examiner*—John Rivell
(74) *Attorney, Agent, or Firm*—Gerald D. Malpass, Jr.

(57) ABSTRACT

A multi-port injection/selection valve utilizes a ferrule cluster to connect tubes or capillaries to a common port in the valve. The use of micro ferrule clusters, as opposed to conventional connectors such as nuts and/or bolts, permits the capillary ends to be positioned in extremely close proximity to the valve rotor and to each other, thus minimizing the volume between two capillaries when they are in brought into fluid communication with each other.

20 Claims, 5 Drawing Sheets

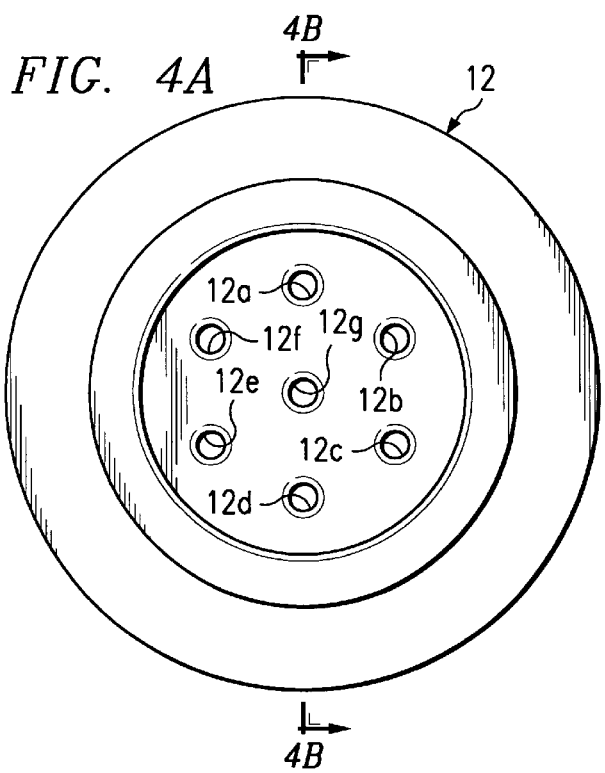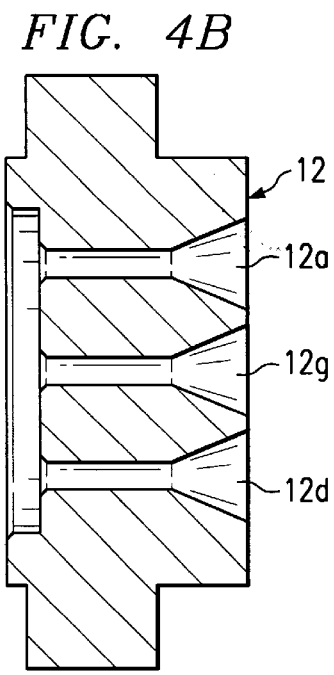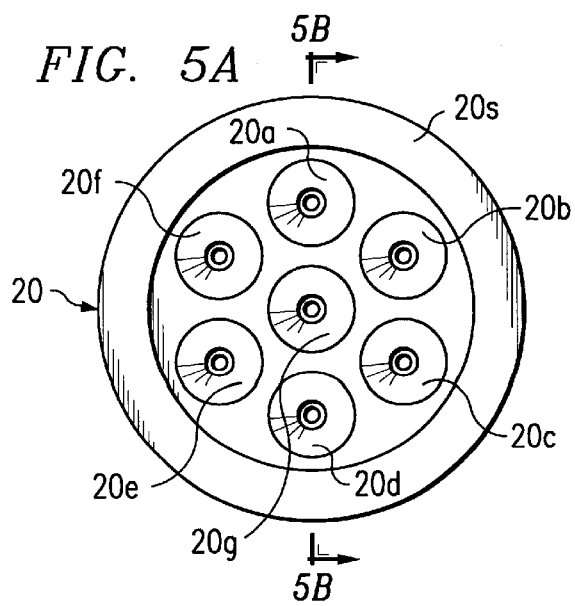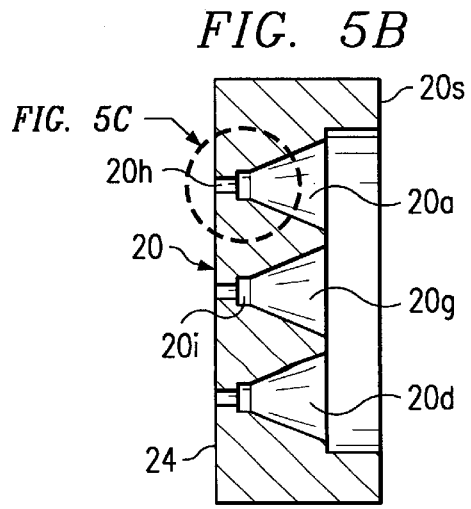

SELECTION VALVE WITH FERRULE CLUSTER

FIELD OF THE INVENTION

This invention relates to a multi-port valve that is used for selection of fluid streams and/or injection of fluids in processes such as liquid chromatography. In particular, the invention relates to an injection/selection valve that utilizes a ferrule cluster to connect tubes or capillaries to a common port in the valve.

BACKGROUND OF THE INVENTION

Multiport selector/injector valves are well known and have been used in a variety of industrial processes, such as liquid chromatography. For example, selection valves are commonly used in liquid chromatography and other analytical methods to direct fluid flow along alternate paths. Such valves are also used to terminate fluid withdrawal from one source and select another source of fluid, for example, such as when a variety of streams in an industrial process is selectively sampled for analysis.

Injector/selector valves are often used in high pressure liquid chromatography (HPLC) or gas chromatography (GC). U.S. Pat. No. 4,242,909 (Gundelfinger '909), which is hereby fully incorporated by reference, describes a sample injection apparatus for withdrawing liquid samples from vials and injecting them into a chromatographic column or other analyzing device. The apparatus is said to minimize wastage, cross contamination, and dilution of the samples, and to be capable of automation with a minimum of complexity. Injector/selector valves are particularly useful in chromatographic applications since a substantial amount of time and effort is required to set up a particular HPLC or GC system, which may often utilize multiple columns and/or multiple detection systems. Multiport selection valves permit the operator of the chromatograph to redirect flows such that particular samples are selected for injection into a particular column, or alternatively, to direct the output from a particular column to one or more different detectors.

As mentioned above, multiport selection valves have been known for some time, including those which utilize a cylindrical rotor and stator combination. In some of these valves, the stator holds the fluid tubes in fixed relation to each other and presents the tube ends to a rotor face which may contain a grooved surface. By varying the angle of the rotor, the tubes are selectively brought into fluid communication. One type of injector/selector valve using a rotor/stator combination is the Type 50 rotary valve from Rheodyne, Incorporated. The Type 50 valves are said to operate by rotation of a flat rotor against a flat stator (see "Operating Instructions for Type 50 Teflon Rotary Valves," Rheodyne, Incorporated, printed in U.S.A. 4/94). Another rotor/stator selector valve is shown in U.S. Pat. No. 5,193,581 (Shiroto, et al.). The valve is said to comprise, among other things, a stator plate having a plurality of outlet holes extending through the stator plate and arranged in a circle concentric with a valve casing, and a rotor having a U-shaped passage formed in the rotor. The rotor is said to be rotated through a desired angle so that an inlet hole can be in fluid communication with selected ones of the outlet holes through the U-shaped passage of the rotor.

U.S. Pat. No. 5,419,419 (Macpherson) describes a rotary selector valve that is used in connection with an automatic transmission in an automobile. A motor is said to index a shear plate of the selector valve to predetermined positions for shifting the transmission. A series of working lines as shown in FIG. 6 are maintained in a closed spatial relationship with the casing.

U.S. Pat. No. 3,494,175 (Cusick, et al.) discloses a valve having a plurality of capillaries which are held in spaced relationship within a manifold plate member. U.S. Pat. No. 3,752,167 (Makabe) discloses a fluid switching device including a plurality of capillaries that are held within threaded holes by couplings. A rotary member allows fluid communication between the tubes. U.S. Pat. No. 3,868,970 (Ayers, et al.) discloses a multipositional selector valve said to be adapted with a means for attaching a plurality of chromatographic columns to the valve, such that the flow can be directed into any of the columns. U.S. Pat. No. 4,705,627 (Miwa, et al.) discloses a rotary valve said to consist of two stator discs and a rotor disposed between the two stator discs. Each time the rotor is turned intermittently it is said, different passages are formed through which the fluid in the valve runs. U.S. Pat. No. 4,722,830 (Urie, et al.) discloses multiport valves. The multiport valves are said to be used in extracting fluid samples from sample loops connected with various process streams.

In many applications using selector/injector valves to direct fluid flows, and in particular in liquid and gas chromatography, the volume of fluids is small. This is particularly true when liquid or gas chromatography is being used as an analytical method as opposed to a preparative method. Such methods often use capillary columns and are generally referred to as capillary chromatography. In capillary chromatography, both gas phase and liquid phase, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

In the design of selector or injector valves with minimal internal volume, the prime design consideration is to bring all of the fluid passages into the closest possible proximity to each other. To do this with conventional capillary connectors is very difficult, since the nuts of the connectors are relatively large and require a fair amount of space. Thus, the valve itself has to be relatively large in order to accommodate the connections.

One solution to the large connectors has been to drill the injector ports on an angle. By angling the injector ports, the ends of the channels can all emerge in close proximity to a common point, while the opposite ends of the channels are sufficiently spaced apart to accommodate the larger connectors. An example of this approach is shown in U.S. Pat. No. 5,419,208 (Schick), which is hereby fully incorporated by reference. However, this approach has certain drawbacks. First, angled holes are difficult to produce and expensive to machine. Further, the angled passage from the capillary connector to the center of the valve stator is longer than it would be if the capillary could be connected directly on the face of the valve in close proximity to other capillaries. This additional length creates additional dead volume, which is undesirable as noted above. A further disadvantage of this approach is that the emerging hole near the center of the valve stator has an elliptical shape, which is not desirable.

Another type of capillary connection is shown in U.S. Pat. No. 4,792,396 (Gundelfinger '396), which is hereby fully incorporated by reference. Gundelfinger '396 describes a frame used as part of an injector said to be useful in loading a sample at high pressure into a chromatographic column. The frame is said to comprise ferrules for sealing tubes, and it is said that a tube coupling hole in the frame can couple to a standard 1/16" tube, but also can couple to a much smaller diameter tube useful for minimizing dispersion when small samples or small chromatographic columns are used. The use of ferrules to make capillary or tubing connections to chromatography apparatus is also shown in, for example, U.S. Pat. Nos. 5,674,388 (Anahara), 5,744,100 (Krstanovic), 5,472,598 (Schick), 5,482,628 (Schick), and 5,366,620 (Schick).

It would be desirable to have a selector/injector valve that can be made with the smallest possible valve volume. There is also a need for an injector/selector valve which brings capillary or tube ends into the closest possible proximity to each other and to the valve stator so that valve dead volume is minimized. Finally, there is also a need for a capillary connector system that can be used to connect capillaries in the closest possible proximity.

SUMMARY OF THE INVENTION

The invention relates to a multi-port injection/selection valve that utilizes one or more ferrule clusters to connect tubes or capillaries to a common port in the valve. The ferrule clusters connect the tubes or capillaries to the body of the valve assembly. The use of ferrule clusters, as opposed to conventional connectors such as nuts and/or bolts, permits the capillary ends to be positioned in extremely close proximity to the valve rotor and to each other, thus minimizing the space between two capillaries when they are in brought into fluid communication with each other (i.e., the "dead volume" in the connection). The ferrule clusters can be made extremely small.

In one embodiment the invention is a valve, comprising: a) a plurality of ferrules formed into one or more ferrule clusters, each of said ferrules having a ferrule through-hole; b) a stator in contact with at least one of said ferrule clusters, said stator having a stator front side and a stator flat surface opposite said front side, said stator front side having a plurality of impressions into which some or all of said ferrules are received, each of said impressions opening to a terminal cylindrical bore (tube pocket), each of said impressions also having a stator through-hole opening onto said stator flat surface; c) a plurality of capillary tubes, each of said capillary tubes extending through at least one of said ferrule through-holes and into a stator impression up to the terminus of said cylindrical bore; d) means for applying pressure to said one or more ferrule clusters; and e) a rotor comprising a stator-contact surface and a fluid communication channel, said stator-contact surface abutting said stator flat surface and being rotatable about an axis to establish fluid communication between selected pairs of capillaries through said fluid communication channel.

In yet other embodiments, the invention is a capillary chromatographic system comprising the valve of the invention. In still other embodiments the invention is a method for carrying out a chromatographic analysis and a method for connecting capillary tubes to a chromatographic system.

BRIEF DESCRIPTION OF THE DRAWINGS

FIGS. 4A, 4B shows one embodiment of the ferrule backup plate of the inventive valve.

FIGS. 5A, 5B shows the ferrule-contact surface of one type of stator useful in the inventive valve, as well as a sectional view of the same stator.

DETAILED DESCRIPTION

Figure 1:
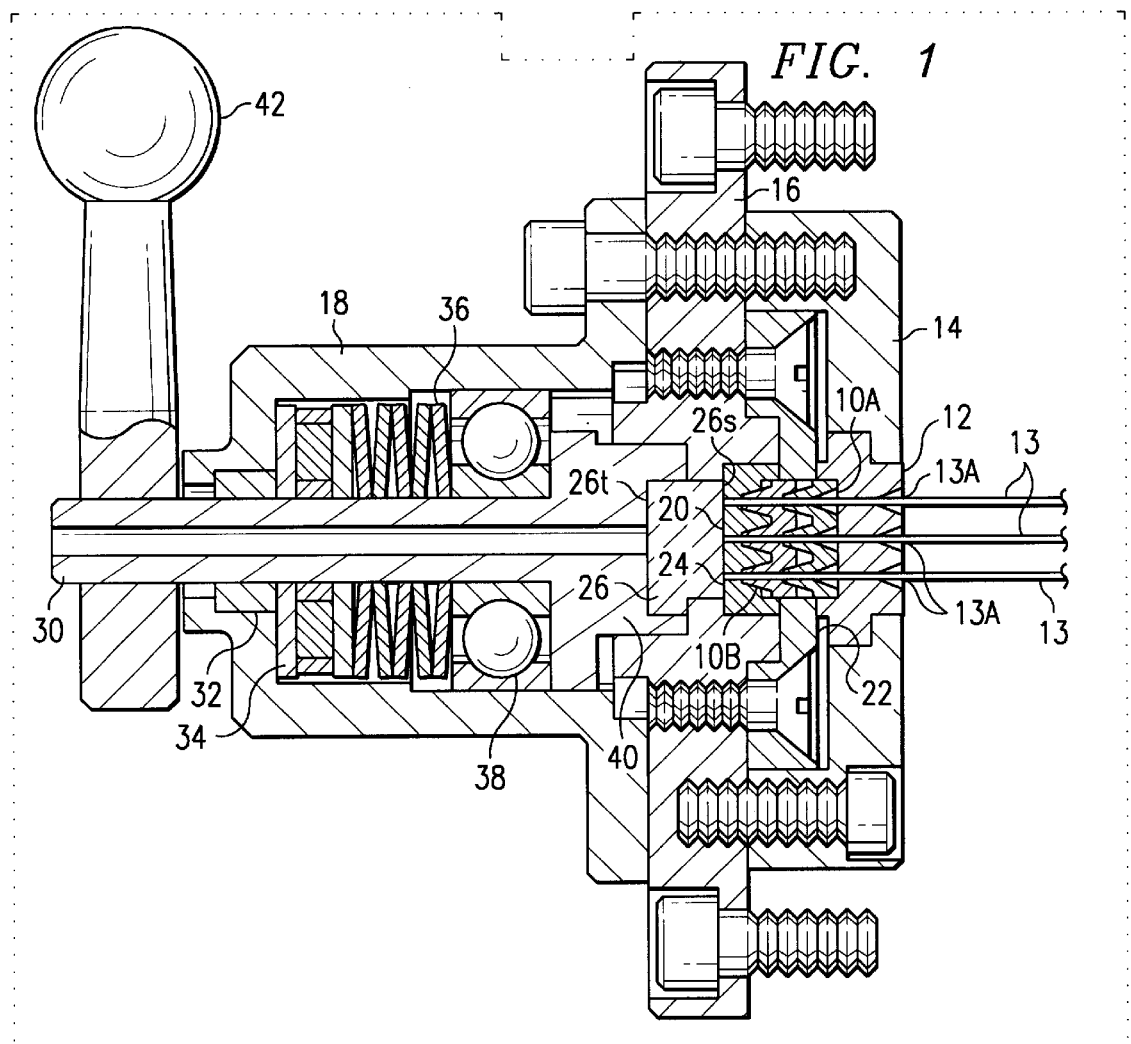
FIG. 1 is a sectional view showing a valve according to one embodiment of the invention.
Figure 2A:
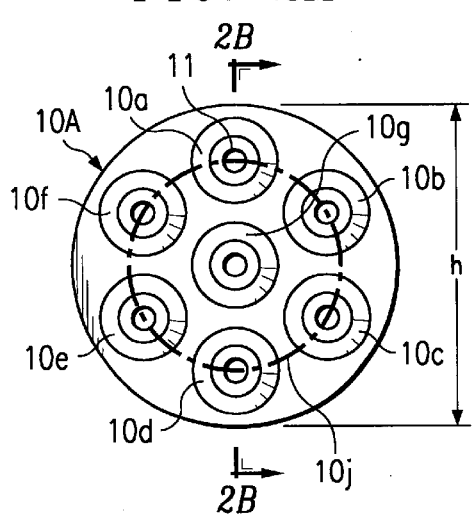
FIGS. 2A, B shows a front view and a sectional view along line AA of one type of ferrule cluster useful in the present invention.
Figure 2B:
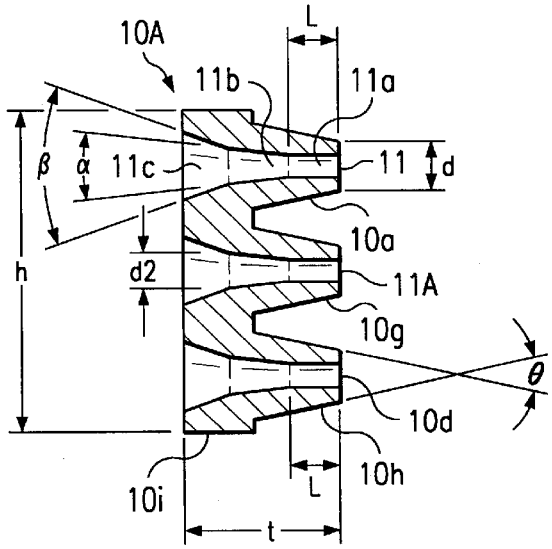
Figure 3A:
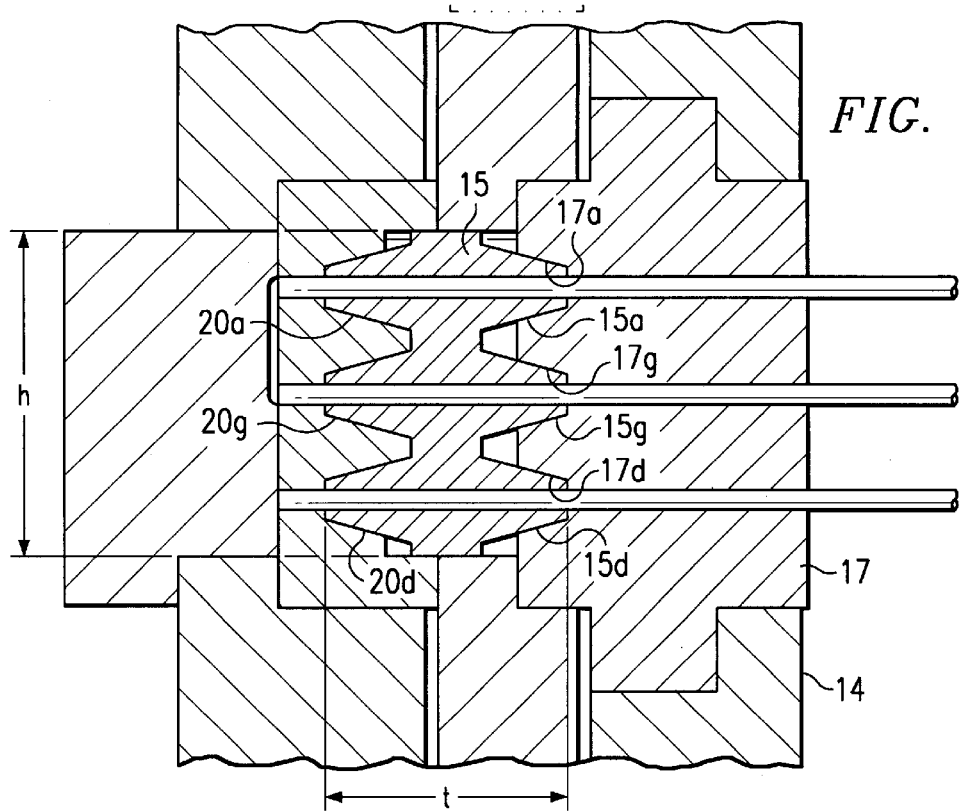
FIGS. 3A and 3B show sectional views of two types of ferrule clusters of the invention positioned within a valve of the invention.

As seen in FIG. 1, one embodiment of the inventive valve comprises a plurality of ferrules formed into two ferrule clusters 10A and 10B. As best shown in FIG. 2, in one embodiment the ferrule clusters, exemplified by 10A, comprise a plurality of ferrules 10a–10g which are integrally formed into a one-piece ferrule cluster as shown in FIG. 2 or FIG. 3A. The ferrules of the invention may be of the single-ended type, as shown in FIG. 1 and 2, or the double-ended type, as best shown in FIG. 3A. The double-ended type approximates two single-ended ferrules with their ends joined. Thus, the double-ended ferrule has tapered gripping portions on both of its ends.

Referring again to FIG. 2, the ferrules are positioned such that there is a single ferrule 10g located at the center of a circle 10j. The remaining ferrules 10a–10f are distributed around the circumference of circle 10j and are centered on said circumference. The ferrules shown in FIG. 2 are of the single-ended type, having a gripping end exemplified by 10h and a compression end exemplified by 10i. The double-ended ferrules shown in FIG. 3A have only two gripping ends. Referring to FIG. 2, the gripping ends of both the single-ended and double-ended ferrules are exemplified by gripping end 10h, which is characterized by a tip diameter d (gripping end tip diameter) as shown in FIG. 2. The single-ended and double-ended ferrules are both characterized also by exterior cone angle θ. When pressure is applied to the compression end of the single-ended ferrule, or to either gripping end of a double-ended ferrule, the gripping ends are all forced into impressions on the valve stator, or into conical portions of the ferrule through-holes (as in the case of stacked ferrule clusters as discussed below), and/or into impressions on the ferrule cluster back-up plate (in the case of the double-ended ferrules, as shown below). This causes the ferrule gripping end tip diameters to be reduced, in turn causing the ferrule gripping ends to "bite" into and hold the capillaries which are disposed in the respective through-holes of the ferrules.

Referring to FIG. 2, each single-ended ferrule has a through-hole, exemplified by through-hole 11, into which a capillary (capillary tube) or other tube is received. The terms "capillary" or "capillary tube" shall be used interchangeably herein, and shall be understood to refer to a tube having and outside diameter of from about 50 to about 1600 microns. In one embodiment of the invention, the ferrule through-holes are as shown in FIG. 2 and comprise a cylindrical portion 11a and first and second conical portions 11b, and 11c, respectively. The diameter of cylindrical portion 11a can be sized as needed to accommodate tubes of any diameter. In some embodiments of the invention, the through-hole cylindrical portion 11a has a diameter of from about 0.30 millimeters (mm) to about 0.45 mm, alternatively from about 0.35 mm to about 0.41 mm, and in yet another alternative from about 0.38 mm to about 0.41 mm. The conical sections of the through-holes each have a wide end and a narrow end, as shown in FIG. 2. The cylindrical portion of through-hole 11 extends along length L of the gripping end 10*h*. The first and second conical sections 11*b* and 11*c* are characterized by interior cone angles α and β. The value of α, θ, and L are not particularly critical, but β is normally about 30 to 45 degrees. In any case, the value of β is adjusted so that a gripping end of another ferrule can be received in second conical section 11*c* when the ferrule clusters are stacked, as discussed below. The second through-hole conical section 11*c* is also characterized by the diameter of its narrow end, d2 (narrow end diameter). This is shown for convenience on through-hole 11A. Naturally, the through-hole diameter of the ferrules can be measured at any point along the length of the through-hole, and in the case of the single-ended ferrules shown in FIG. 2 the diameter will vary in the first and second conical portions 11*b* and 11*c*, depending on where along the through-hole the measurement is made. As for the double-ended ferrule through-holes, the through-hole diameter may vary, but the through-holes preferably have a uniform diameter along the length of the through-hole. In one embodiment of the inventive valve, the ferrule through-holes have a maximum diameter at any point along the through-hole of from about 0.35 mm to about 0.90 mm, or from about 0.45 mm to about 0.80 mm, or from about 0.55 mm to about 0.70 mm, alternatively from about 0.65 mm to about 0.70 mm. While the ferrules shown in FIG. 2, FIG. 3A, and FIG. 3B have a specific shape, the ferrules useful in the inventive valve may have any number of exterior shapes and/or through-hole geometries, as long as the ferrules perform the usual function of a ferrule, namely gripping the capillary or tube inserted through the ferrule when compressive forces are applied to the ferrule.

Figure 3B:
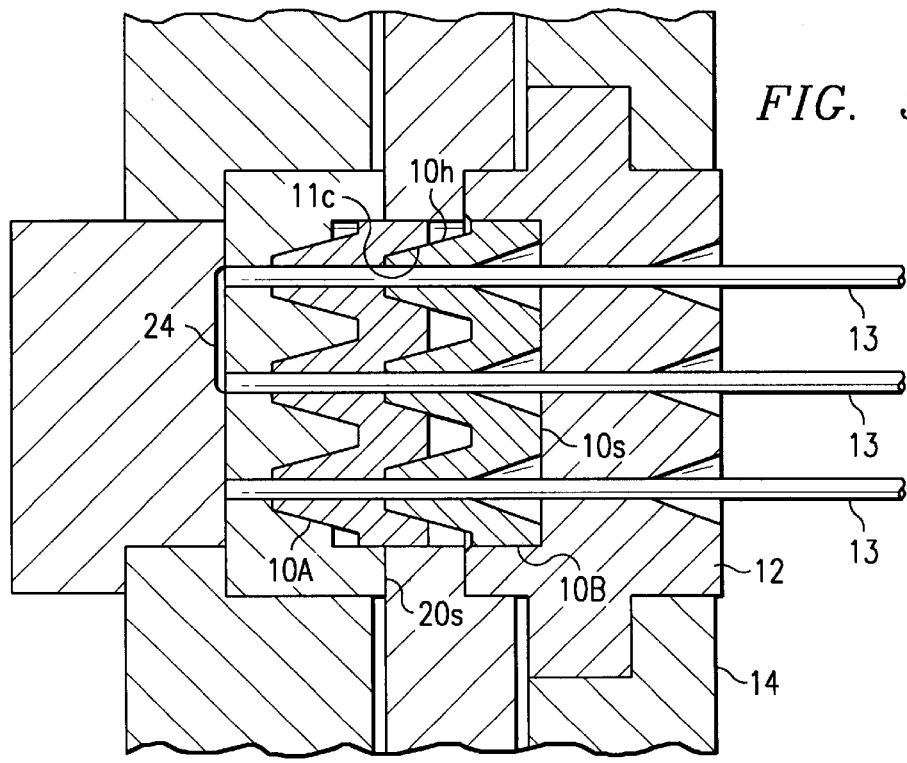

The inventive valve comprises one double-ended ferrule cluster or one or more single-ended ferrule clusters. When two or more single-ended ferrule clusters are employed, they are preferably arranged in a "stacked" configuration. Referring again to FIG. 1, the two ferrule clusters 10A and 10B are shown in a stacked arrangement The detail of this arrangement is best shown in FIG. 3B. In the stacked ferrule cluster arrangement using two ferrule clusters, a second cluster 10B is positioned behind a first cluster 10A. The capillaries 13 extend through the ferrule through-holes in both clusters, and the ferrule gripping ends exemplified by 10*h* of second cluster 10B are received and compressed in the second conical sections, exemplified by 11*c*, of the ferrules in ferrule cluster 10A Thus, each of the capillaries 13 is gripped by two ferrule gripping ends. Naturally, three or more clusters may be stacked in the fashion shown in FIG. 3B.

Referring again to FIG. 1, a ferrule back-up plate 12, best shown in FIG. 4, holds the stacked ferrule clusters 10A and 10B in place and transmits compressive forces to the ferrules so that they grip the capillaries 13 inserted through them. Referring to FIG. 4, the back-up plate is supplied with through-holes 12*a*–12*g*, corresponding to ferrule through-holes 10*a*–10*g* on ferrule clusters 10A and 10B. Through-holes 12*a*–12*g* are positioned so that the capillary tubes may pass through them in order to be received in the ferrule through-hole openings. Referring to FIG. 3B, the backup plate 12 is placed against the flat side 10*s* of the ferrule cluster 10B and is adapted to transmit compressive forces to the ferrule clusters so that the ferrules are compressed and thus grip the individual capillary tubes placed in each ferrule. In one embodiment of the invention, the compressive force is supplied through the ferrule compression plate 14 shown in FIGS. 1 and 3. The compression plate 14 is bolted to a base plate 16 and contacts the ferrule back-up plate 12 thus urging the back-up plate against the ferrule cluster as the bolts are tightened. The base plate in turn is secured to a bearing assembly housing 18. However, it should be clear that any means for applying pressure to the ferrules and ferrule cluster may be employed. Such means may, for example, utilize pressure supplied by hydrostatic (including any pressurized liquid), electromagnetic, or pneumatic sources, in addition to pressure supplied by the tightening of threaded connections and the like as exemplified in FIG. 1.

Figure 5C:
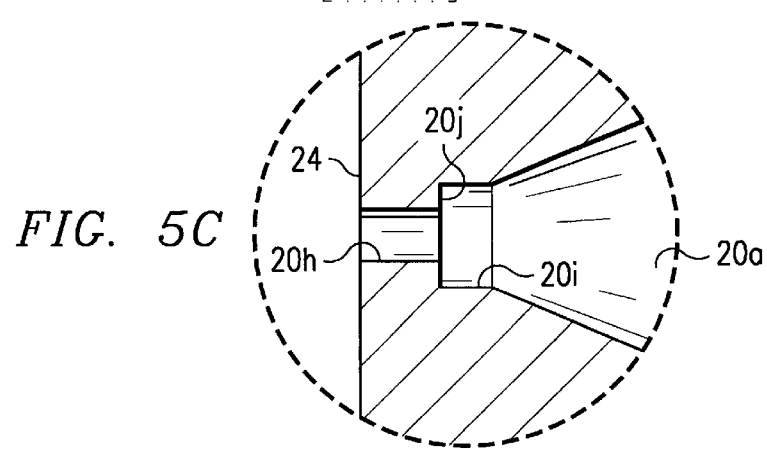
FIG. 5C shows an enlarged sectional view of a portion of the stator shown in FIG. 5.

Referring again to FIG. 1., a valve stator 20 is held in place by a stator hold down plate 22 and receives the capillaries 13. As best shown in FIG. 5, the valve stator 20 has a stator front side 20*s* comprising a plurality of conical impressions 20*a*–20*g* for receiving the ferrules of ferrule cluster 10A. Each conical impression opens to a terminal cylindrical bore, alternatively referred to herein as a "tube pocket," exemplified by 20*i*. Each conical impression also has a through-hole, exemplified by 20*h*, which opens onto the flat stator surface 24.

FIG. 5A shows an enlarged sectional view of conical impression 20*a*, which is exemplary of the other conical impressions. As shown in FIG. 5A, conical impression 20*a* opens to a tube pocket 20*i*, the tube pocket 20*i* having a terminus coincident with surface 20*j*. Through-hole 20*h* extends from surface 20*j* and opens onto stator flat surface 24. In normal use, a capillary tube (not shown in FIG. 5A) would extend through one or more ferrule through-holes (also not shown), then through conical impression 20*a* and into tube pocket 20*i* up to stator through-hole 20*h* so that the end of the capillary is substantially flush with the terminus of the tube pocket at surface 20*j*. Fluid emerging from the capillary can then pass into stator through-hole 20*h* and emerge at stator flat surface 24.

Referring again to FIG. 3B, the capillary tubes 13 emerge from the ferrule through-holes and extend up to the stator through-holes so that the ends of the capillaries are, as noted above, substantially flush with the terminus of a tube pocket. The capillary ends disposed in the tube pockets are naturally in the same relative positions in which the ferrules are arranged on the ferrule clusters. That is, the capillary ends are distributed on the stator evenly around the circumference of a circle having a single capillary end located at the center of the circle.

Figure 6A:
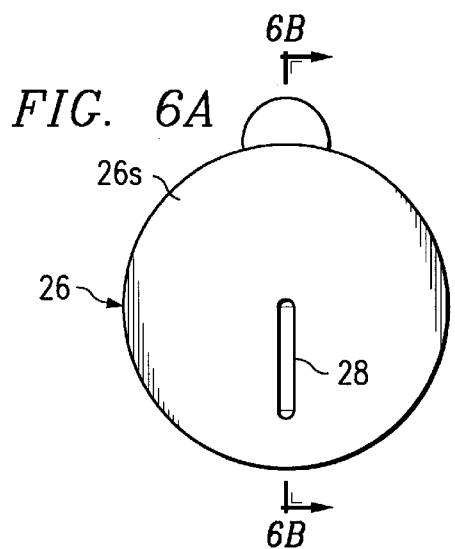
FIGS. 6A, 6B and FIGS. 7A, 7B show the stator-contact surface of two different embodiments of the valve rotor, as well as a sectional views of said rotor embodiments.
Figure 6B:
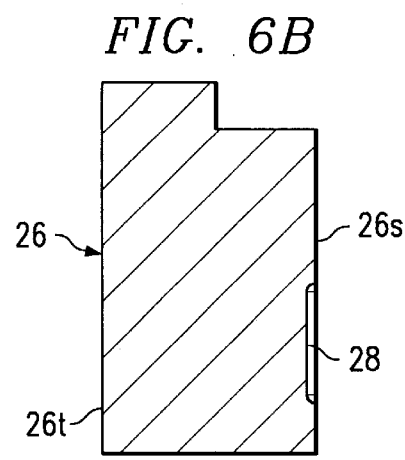
Figure 7A:
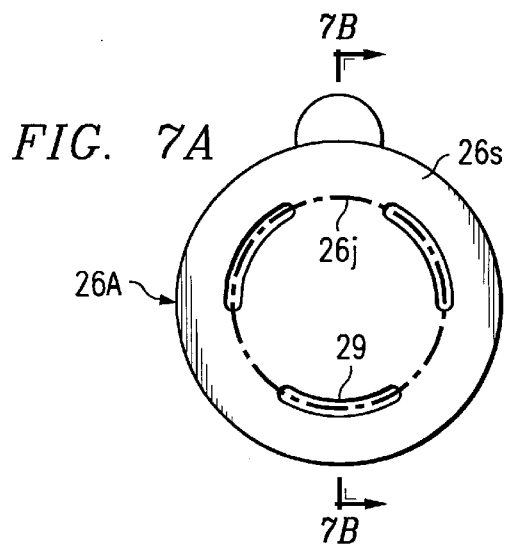
Figure 7B:
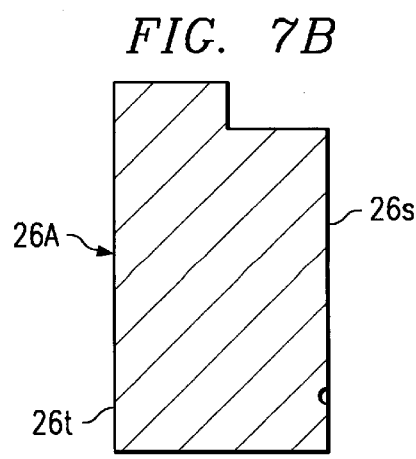

Referring once more to FIG. 1, the valve shown therein comprises a rotor 26 which abuts the stator 20. The rotor may be of any number of types, two of which are shown in FIG. 6 and FIG. 7. Referring to FIG. 6, the rotor shown therein has a grooved stator contact surface 26*s* and a rotor shaft contact surface 26*t*. A single groove 28 is cut into the stator contact surface 26*s*. Referring to FIG. 7, an alternative rotor 26A is shown with three grooves, exemplified by groove 29. The grooves define arcs lying along the circumference of a circle 26*j*. As shown in FIG. 1, the stator contact surface 26*s* abuts the stator flat surface 24. Continuing to refer to FIG. 1, the rotor shaft contact surface is connected to a rotor shaft 30 for varying the angle of the rotor with respect to the stator. By rotating the rotor surface 26*s*, the rotor groove(s) may be selectively positioned to establish fluid communication between specific pairs of capillaries 13. In the case of the rotor shown in FIG. 6, one end of the single groove 28 is always aligned with, and in fluid communication with, the center through-holes of the ferrule cluster back-up plate, ferrule clusters, and stator (12*g*, 10*g*, and 20g). As the rotor is rotated, fluid communication may be selectively established between the center capillary and any one the capillaries disposed in ferrule through-holes 10a through 10f.

The rotor shown in FIG. 7 may be used when it is desired to establish fluid communication between various pairs of the capillaries disposed in ferrule through-holes 10a through 10f.

While the rotors shown in FIG. 6 and FIG. 7 use grooves cut into the rotor surfaces to permit fluid communication between various capillaries, any type fluid communication channel could be provided on the rotor. For example, rather than grooves, a channel could be cut in the body of the rotor so that it has one opening at the center of the rotor and another opening lying along the circle circumference 26j. However, to minimize the dead volume of the valve, grooves cut into the surface of the rotor are preferred as rotor fluid communication channels.

Returning to FIG. 1, rotor shaft 30 is connected to rotor surface 26t and is supported by bearing bushing 32, roller thrust bearing 34, and radial ball bearing 38. A set of Belleville springs 36 is used to bias the rotor shaft and rotor 26 toward the stator 20. A rotor driver pin 40 engages the rotor, and a handle 42 is used for operating the rotor if manual rotation thereof is desired. Obviously, any number of automatic means for rotating the rotor could be connected to the rotor shaft.

Figure 8:
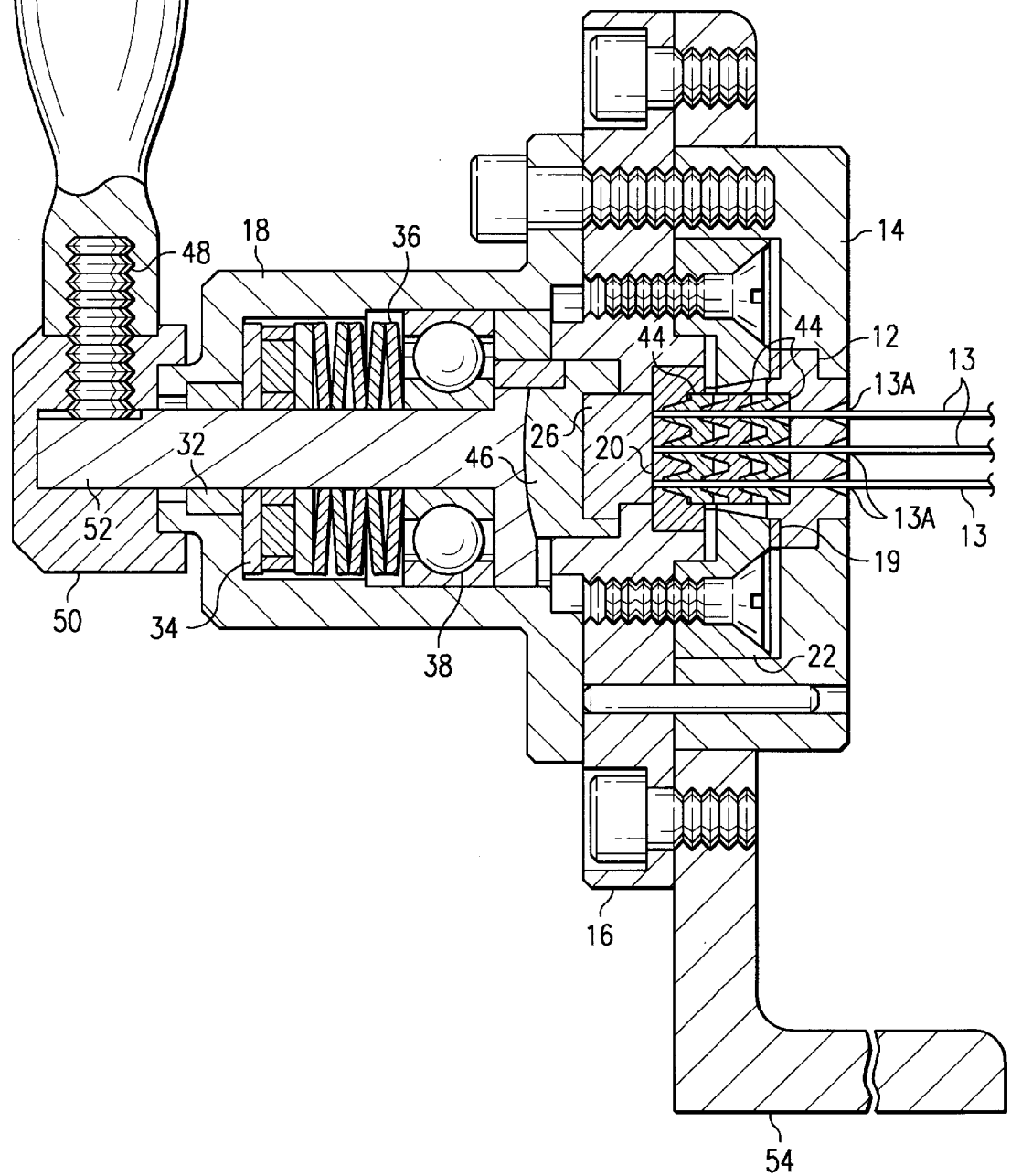
FIG. 8 shows a sectional view of another valve of the invention.

FIG. 8 shows an alternative embodiment of the inventive valve which comprises three stacked ferrule clusters 44 and rotor mount 46 in place of the rotor drive pin shown in FIG. 1. Also, the handle comprises handle portion 46, threaded connection 48, and collar 50 attached to rotor shaft 52. The valve in FIG. 8 is shown mounted to a mounting bracket 54. Also included in the valve of FIG. 8 is a Kel-F® (Kel-F is a registered trademark assigned to Dyneon LLC) washer 19 disposed between the ferrule compression plate 14 and base plate 16. The other parts are as shown in FIG. 1.

FIGS. 3A and 3B illustrate, as noted above, alternate methods of connecting the capillaries in the inventive valve. In Method A, shown in FIG. 3A, double-ended ferrules are used in a single cluster 15; in Method B, which is used in the valve shown in FIG. 1, single-ended ferrules are used in a double cluster. In both methods, each capillary connection is held in place by two ferrule gripping ends. Referring to FIG. 3A, when Method A is used the double-ended ferrules 15a–15g are arranged in the ferrule cluster 15 in a pattern similar to that shown for the single-ended ferrules 10a–10g in FIG. 2. In FIG. 3A, only double-ended ferrules 15a, 15g, and 15d are shown in the sectional view of the double-ended ferrule cluster 15. When method A is used, a different ferrule back-up plate 17 is utilized. Ferrule back-up plate 17 is provided with conical impressions 17a–17g, of which only 17a, 17g, and 17d are visible in the sectional view. The conical impressions in the ferrule back-up plate 17 correspond to double-ended ferrules 15a–15g, and each receives one end of a double-ended ferrule in a fashion similar to the way in which stator conical impressions 20a–20g, fully shown in FIG. 5, receive the opposite end of the double-ended ferrule.

Whether double-ended or single-ended ferrules are used, the individual ferrules, including the single central ferrule if present, are preferably joined together as part of an integral, one-piece ferrule cluster. That is, the ferrule cluster is a one-piece cluster that is not adapted to be disassembled into multiple pieces. Such one-piece clusters can be formed, for example, by compression molding of plastic materials to form a plastic part, or by machining a piece of solid bar stock. Alternatively, an integral ferrule cluster as defined herein could be formed by fusing, gluing, soldering, welding, or using like operations to join multiple pieces of material to form a single part. Referring again to FIG. 2, in one embodiment of the invention, the ferrule clusters may be generally described as circular plates (although it need not be circular) having individual ferrules integrally formed thereon. Naturally, non-integral ferrule clusters could also be used, such as when individual ferrules are belted, bolted, screwed, or wired together to form a cluster.

While the specific embodiments of the inventive valve shown in FIG. 1 through FIG. 8 utilize certain numbers of ferrules arranged in particular ways in the cluster, the inventive valve and methods disclosed herein may generally employ any plurality of ferrules arranged in any useful pattern in the ferrule cluster.

The ferrule clusters may be fabricated form any suitable material, including thermoset materials and thermoplastics. Polyether-ether ketone (PEEK) is a particularly suitable thermoplastic material for fabricating the ferrule clusters of the invention. The rotor and stator of the inventive valve may be fabricated from any suitable material, for example, metal, plastic materials, ceramic materials, or zirconia In a preferred embodiment, the rotor and stator are ceramic or zirconia.

The valve of the instant invention may be fabricated to any useful size. However, the inventive valve is particularly useful in micro applications, in particular those utilizing fluid flow rates of 0.5 ml/min or less. Typically this includes capillary chromatography. As used herein, and for the purpose of interpreting the claims of this patent specification, the terms "capillary chromatographic system" and "capillary chromatography" shall be understood to refer to a chromatograph, or chromatographic analyses performed thereon, respectively, which employ(s) one or more capillary columns. As used herein, "capillary column" means a capillary (capillary tube) having a length greater than or equal to 25 meters, wherein the capillary has an outside diameter from about 50 to about 1600 microns. It will be understood that the capillaries which may be connected to the inventive valve need not be "capillary columns," although they may be. For example, some of the capillaries may be shorter capillaries which are used to feed or transfer fluids to a capillary column. Those skilled in the art will understand that the term "chromatographic analysis" refers not only to the separation or partial separation of mixtures into their individual components, but also to methods in which a single, pure material is analyzed. In the latter situation, it may technically be the case that no "separation" occurs, because only a single, pure component is present. Further, as noted above a distinction is sometimes made between chromatographic methods which are performed for analytical purposes and those which are performed for preparative purposes. However, for convenience, the term "chromatographic analysis" as used herein will be understood to include separations and methods which are conducted for both analytical and preparative purposes.

Capillary chromatography has long been known for extremely high resolution, and it can be carried out using both gas and liquid mobile phases. In this sense the term "fluid" will be understood, as it normally is, to include both liquids and gases. The valve of the present invention is also useful in high pressure liquid chromatographic (HPLC) applications, including capillary HPLC. Thus, one embodiment of the invention is a capillary chromatographic system, including gas chromatographs and liquid chromatographs, comprising the valve of the invention.

While the inventive valve and its components may be sized in any useful manner, certain valve and valve component dimensions are preferred. Referring to FIG. 2 and FIG. 3A, the ferrule clusters of the invention, both single-ended and double-ended, are also characterized by a height "h" and a ferrule cluster thickness "t." In the case of the double-ended ferrules, "t" extends from one gripping end tip to the other, as shown in FIG. 3A. Preferably, the ferrule cluster height h is from 4 millimeters (mm) to about 8 mm, more preferably from about 5 mm to about 7 mm, and most preferably from about 5.5 mm to about 6.5 mm. Similarly, the ferrule cluster thickness t is preferably from about 2 mm to about 6 mm, more preferably from about 3 mm to about 5 mm, and most preferably from about 3.5 mm to about 4.5 mm. Referring again to FIG. 2, for both the single-ended and double-ended type of ferrule, the dimension d (gripping end tip diameter), is preferably from about 0.5 mm to about 1.00 mm, more preferably from about 0.75 mm to about 0.95 mm, and most preferably from about 0.85 mm to about 0.90 mm. The narrow end of the second through-hole conical section, d2, is preferably from about 0.5 mm to about 0.8 mm, more preferably from about 0.55 mm to about 0.75 mm, and most preferably from about 0.60 mm to about 0.70 mm.

In another embodiment of the invention, the capillaries 13 are fused silica capillaries having an outside diameter of about 365 microns. In other embodiments, the outside diameter of the capillaries is between about 100 and 500 microns, and preferably between about 250 and 400 microns.

In yet another embodiment, the present invention is a method for carrying out a chromatographic analysis, comprising: a) providing a plurality of ferrules formed into one or more ferrule clusters, each of said ferrules having a ferrule through-hole; b) placing a stator in contact with at least one of said ferrule clusters, said stator having a stator front side and a stator flat surface opposite said front side, said stator front side having a plurality of impressions into which some or all of said ferrules are received, each of said impressions opening to a tube pocket, each of said impressions also having a stator through-hole opening onto said stator flat surface; c) disposing a plurality of capillary tubes through said ferrule through-holes and into said tube pockets; d) applying pressure to said one or more ferrule clusters; e) placing in contact with said stator a rotor comprising a stator-contact surface and a fluid communication channel such that said stator-contact surface abuts said stator flat surface and is rotatable about an axis to establish fluid communication between selected pairs of capillaries through said fluid communication channel; f) placing one or more of said capillaries in fluid communication with a capillary column; g) rotating said rotor to establish fluid communication between said capillary column and one or more of said capillaries; and h) passing a fluid through one or more of said capillaries and into said capillary column. In yet a further embodiment, the present invention is an automated method or automated chromatographic system for carrying out a chromatographic analysis using the valve of the invention.

In still another embodiment, the present invention is a method for connecting capillaries to a chromatographic system, the method comprising: a) providing a plurality of ferrules formed into one or more ferrule clusters, each of said ferrules having a ferrule through-hole; b) disposing a plurality of capillary tubes through said ferrule through-holes; c) providing a plurality of impressions into which said some or all of ferrules are received, each of said impressions having a tube pocket into which one of said capillary tubes extends; and d) applying pressure to said one or more ferrule clusters.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. Hence, the embodiment and specific dimensions, materials and the like are merely illustrative and do not limit the scope of the invention or the claims herein.

I claim:

1. A valve, comprising:
   a) a plurality of ferrules formed into one or more ferrule clusters, each of said ferrules having a ferrule through-hole;
   b) a stator in contact with at least one of said ferrule clusters, said stator having a stator front side and a stator flat surface opposite said front side, said stator front side having a plurality of impressions into which some or all of said ferrules are received, each of said impressions opening to a tube pocket, each of said impressions also having a stator through-hole opening onto said stator flat surface;
   c) a plurality of tubes, each of said tubes extending through at least one of said ferrule through-holes and into a stator impression up to the terminus of said tube pocket;
   d) means for applying pressure to said one or more ferrule clusters; and
   e) a rotor comprising a stator-contact surface and a fluid communication channel, said stator-contact surface abutting said stator flat surface and being rotatable about an axis to establish fluid communication between selected pairs of tubes through said fluid communication channel.

2. The valve of claim 1 wherein said ferrule through-holes comprise first and second conical sections and a cylindrical section, said cylindrical section having a diameter from about 0.38 mm to about 0.41 mm.

3. The valve of claim 2 wherein said second conical section has a narrow end diameter of from about 0.6 mm to about 0.7 mm.

4. The valve of claim 3 wherein each of said ferrules has a gripping end tip diameter of from about 0.85 to about 0.90 mm.

5. The valve of claim 1 wherein said one or more ferrule clusters comprise a plurality of ferrules distributed along the circumference of a circle and having a single ferrule positioned at the center of said circle.

6. The valve of claim 1 wherein said ferrule clusters are integrally formed.

7. The valve of claim 1 wherein said ferrules have through-holes having a maximum diameter at any point along the through-hole of from 0.35 mm to 0.90 mm.

8. The valve of claim 1 wherein said valve comprises a single, double-ended ferrule cluster.

9. The valve of claim 1 wherein said valve comprises two or three single-ended ferrule clusters.

10. The valve of claim 1 wherein said fluid communication channel comprises a groove formed on said stator contact surface.

11. The valve of claim 1 wherein said one or more ferrule clusters have a ferrule cluster height of from about 5.5 mm to about 6.5 mm.

12. The valve of claim 1 wherein said one or more ferrules clusters have a ferrule thickness of about 3.5 mm to about 4.5 mm.

13. The valve of claim 1 wherein said tubes are fused silica capillary tubes having an outside diameter between about 250 and 400 microns.

14. The valve of claim 1 wherein said ferrules and said ferrule clusters are fabricated from polyether-ether ketone.

15. The valve of claim 14 wherein said stator and rotor are fabricated from zirconia or ceramic.

16. The valve of claim 1 wherein said means for applying pressure to said one or more ferrules clusters comprises a compression plate and a ferrule back-up plate, said compression plate being in contact with and urging said back-up plate against said one or more ferrule clusters in response to the tightening of a threaded connection.

17. A capillary chromatographic system comprising a valve, said valve comprising:
 a) a plurality of ferrules formed into one or more ferrule clusters, each of said ferrules having a ferrule through-hole;
 b) a stator in contact with at least one of said ferrule clusters, said stator having a stator front side and a stator flat surface opposite said front side, said stator front side having a plurality of impressions into which some or all of said ferrules are received, each of said impressions opening to a tube pocket, each of said impressions also having a stator through-hole opening onto said stator flat surface;
 c) a plurality of capillary tubes, each of said capillary tubes extending through at least one of said ferrule through-holes and into a stator impression up to the terminus of said tube pocket;
 d) means for applying pressure to said one or more ferrule clusters; and
 e) a rotor comprising a stator-contact surface and a fluid communication channel, said stator-contact surface abutting said stator flat surface and being rotatable about an axis to establish fluid communication between selected pairs of capillary tubes through said fluid communication channel.

18. A method for carrying out a chromatographic analysis, comprising:
 a) providing a plurality of ferrules formed into one or more ferrule clusters, each of said ferrules having a ferrule through-hole;
 b) placing a stator in contact with at least one of said ferrule clusters, said stator having a stator front side and a stator flat surface opposite said front side, said stator front side having a plurality of impressions into which some or all of said ferrules are received, each of said impressions opening to a tube pocket, each of said impressions also having a stator through-hole opening onto said stator flat surface;
 c) disposing a plurality of capillary tubes through said ferrule through-holes and into said tube pockets;
 d) applying pressure to said one or more ferrule clusters;
 e) placing in contact with said stator a rotor comprising a stator-contact surface and a fluid communication channel such that said stator-contact surface abuts said stator flat surface and is rotatable about an axis to establish fluid communication between selected pairs of capillaries through said fluid communication channel;
 f) placing one or more of said capillaries in fluid communication with a capillary column;
 g) rotating said rotor to establish fluid communication between said capillary column and one or more of said capillaries; and
 h) passing a fluid through one or more of said capillaries and into said capillary column.

19. A method for connecting capillaries to a chromatographic system, comprising:
 a) providing a plurality of ferrules formed into one or more ferrule clusters, each of said ferrules having a ferrule through-hole;
 b) disposing a plurality of capillary tubes through said ferrule through-holes;
 c) providing a plurality of impressions into which some or all of said ferrules are received, each of said impressions having a tube pocket into which one of said capillary tubes extends; and
 d) applying pressure to said one or more ferrule clusters.

20. The method of claim 19 wherein said ferrule clusters are integrally formed and comprise a plurality of ferrules distributed along the circumference of a circle having a single ferrule positioned at the center of said circle, each of said ferrule clusters having a height of from about 5.5 mm to about 6.5 mm and a thickness of about 3.5 mm to about 4.5 mm, said ferrules having a gripping end tip diameter of from about 0.85 to about 0.90 mm, said ferrule through-holes having a maximum diameter at any point along said through-hole of from about 0.35 mm to about 0.90 mm, each of said ferrule through-holes comprising a first conical section, a second conical section, and a cylindrical section, said cylindrical section having a diameter from about 0.38 mm to about 0.41 mm, said second conical section having a narrow end diameter of from about 0.6 mm to about 0.7 mm.

* * * * *